United States Patent
Wen et al.

(10) Patent No.: US 9,012,459 B2
(45) Date of Patent: Apr. 21, 2015

(54) MONOHYDRATE CRYSTALLINE FORM OF 3-(5-(4-(3-FLUOROPROPYL)-PIPERAZIN-1-YL)BENZIMIDAZOL-2-YL)-1-AZAAZULEN-2-ONE, PREPARATION, AND PHARMACEUTICAL COMPOSITION THEREOF

(71) Applicant: Industrial Technology Research Institute, Hsinchu (TW)

(72) Inventors: Yen-Fang Wen, Miaoli County (TW); Yuan-Jang Tsai, Hsinchu County (TW); Wan-Ru Chen, Nantou County (TW); Tsan-Lin Hu, Jhubei (TW); Chia-Mu Tu, Taipei (TW); Chih-Peng Liu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/968,089

(22) Filed: Aug. 15, 2013

(65) Prior Publication Data
US 2014/0171443 A1    Jun. 19, 2014

(30) Foreign Application Priority Data

Dec. 18, 2012    (TW) .............................. 101147995 A

(51) Int. Cl.
*A61K 31/4965* (2006.01)
*C07D 403/04* (2006.01)

(52) U.S. Cl.
CPC .................................. *C07D 403/04* (2013.01)

(58) Field of Classification Search
None
See application file for complete search history.

(56) References Cited

U.S. PATENT DOCUMENTS 7,087,626 B2    8/2006  Beight et al.
7,262,302 B2    8/2007  Mercep et al.
2010/0280012 A1* 11/2010 Lee .............................. 514/218

FOREIGN PATENT DOCUMENTS

TW        201038556 A1    11/2010

OTHER PUBLICATIONS

D.E. Bugay, "Characterization of the solid-state: spectroscopic techniques," Advanced Drug Delivery Reviews, 48, (2001), pp. 43-65.
T. Detoisen et al., "A Rapid Method for Screening Crystallization Conditions and Phases of an Active Pharmaceutical Ingredient," Org. Process Res. Dev., Sep. 9, 2009, 13 (6), pp. 1338-1342.
J.D. Dunitz et al., "Disappearing Polymorphs," Acc. Chem. Res., 1995, 28, pp. 193-200.
D. Giron, "Thermal analysis and calorimetric methods in the characterisation of polymorphs and solvates," Thermochimica Acta 248 (1995), pp. 1-59.
K. Fuji et al., "Physicochemical Understanding of Polymorphism and Solid-State Dehydration/Rehydration Processes for the Parmaceutical Material Acrinol, by Ab Initio Powder X-ray Diffraction Analysis and Other Techniques," J. Phys. Chem. C 2010, 114, pp. 580-586.
M. Sacchetti, "Determining the relative physical stability of anhydrous and hydrous crystal forms of GW2016," International Journal of Pharmaceutics, 273, (2004), pp. 195-202.
M.L. Petersen et al, "Iterative High-Throughout Polymorphism Studies on Acetaminophen and an Experimentally Derived Structure for Form III," J.Am.Che.Soc., 2002, 124, pp. 10958-10959.
T. Detoisien et al., "Thermal analysis: A further step in characterizing solid forms obtained by screening crystallization of an API." International Journal of Pharmaceutics, 403, (2011), pp. 29-36.
S.R. Chemburkar et al., "Dealing with the Impact of Ritonavir Polymorphs on the Late Stages of Bulk Drug Process Development," Organic Process Research & Development, 2000, 4, pp. 413-417.
C.R. Gardner, "Drugs as Materials: Valuing Physical Form in Drug Discovery," Nature Reviews, Drug Discovery, vol. 3, Nov. 2004, pp. 926-934.

* cited by examiner

Primary Examiner — Wu-Cheng Winston Shen
Assistant Examiner — Jean Cornet
(74) Attorney, Agent, or Firm — Muncy, Geissler, Olds & Lowe, P.C.

(57) ABSTRACT

The disclosure is directed to a monohydrate crystalline form of 3-(5-(4-(3-fluoropropyl)piperazin-1-yl)benzimidazol-2-yl)-1-azaazulen-2-one, possessing diffraction peaks of about 12.9°, 15.9°, 17.9°, 21.2°, 22.9°, 23.5° and 24.5°. Its preparation method and pharmaceutical composition thereof are also provided.

17 Claims, 17 Drawing Sheets

|  | formula I (capsule/oral) 30 mg/kg | formula II (0.5% suspension/oral) 30 mg/kg | #4 (0.5% suspension/oral) 30 mg/kg |
| --- | --- | --- | --- |
| $C_{max}$ (ng/ml) | 1,419 ± 1,115 | 1,628 ± 681 | 1,827 ± 250 |
| $T_{max}$ (hour) | 4 ± 1.7 | 6 ± 1.7 | 5 ± 0 |
| $T_{1/2}$ (hour) | 9.9 ± 2.4 | 9.9 ± 0.7 | 16.1 ± 8.9 |
| AUC (hour*ng/ml) | 25,531 ± 23,582 | 29,776 ± 13,849 | 34,757 ± 1,460 |

FIG. 10A

MONOHYDRATE CRYSTALLINE FORM OF 3-(5-(4-(3-FLUOROPROPYL)-PIPERAZIN-1-YL)BENZIMIDAZOL-2-YL)-1-AZAAZULEN-2-ONE, PREPARATION, AND PHARMACEUTICAL COMPOSITION THEREOF

CROSS REFERENCE TO RELATED APPLICATIONS

This application claims priority of Taiwan Patent Application No. 101147995, filed on Dec. 18, 2012, the entirety of which is incorporated by reference herein.

TECHNICAL FIELD

The disclosure relates to a novel crystalline form of 3-(5-(4-(3-fluoropropyl)piperazin-1-yl)benzimidazol-2-yl)-1-azaazulen-2-one, preparation thereof, and a pharmaceutical composition including the crystalline form thereof.

BACKGROUND

Studies in modern molecular biology have discovered that a lot of kinases play an important role in the process of cell growth and cell division, and some other studies have proved that the overexpression of kinases involves cell oncogenesis, cancer cell over-proliferation, cell malignancy, and metastasis. As such, developing kinase inhibitors as effective anti-cancer medications has become an important aim in the field of anti-cancer drug research and development. Currently, the drug industry all over the world has invested greatly in order to develop novel kinase inhibitors, and therefore there are several kinase-inhibitor-based anti-cancer drugs on the market, such as Novartis's Gleevec, AastraZeneca's Iressa and Pfizer's Sutent which have been approved to be clinically effective and have high market share. The azaazulene compound, 3-(5-(4-(3-fluoropropyl)piperazin-1-yl)benzimidazol-2-yl)-1-azaazulen-2-one, is a kind of small-molecule kinase inhibitor, which is capable of inhibiting a plurality of kinases. Therefore, it may be used as the anti-cancer drug and diagnostic reagent in the future.

Different crystalline forms of a specific drug might result in variations of solubility, melting point, stability, bioavailability, and the like. Therefore, it is desirable that a novel crystalline form of the azaazulene compound with homogeneity, stability, reproducibility, and processability should be found for further development.

SUMMARY

The disclosure is directed to a monohydrate crystalline form of 3-(5-(4-(3-fluoropropyl)piperazin-1-yl)benzimidazol-2-yl)-1-azaazulen-2-one, possessing diffraction peaks of about 12.9°, 15.9°, 17.9°, 21.2°, 22.9°, 23.5° and 24.5°.

The disclosure also provides a method of preparing the monohydrate crystalline form of 3-(5-(4-(3-fluoropropyl)piperazin-1-yl)benzimidazol-2-yl)-1-azaazulen-2-one, including: dissolving an amorphous form of 3-(5-(4-(3-fluoropropyl)piperazin-1-yl)benzimidazol-2-yl)-1-azaazulen-2-one of Formula I in dimethyl sulfoxide to form a solution, wherein the weight ratio of the compound of Formula I to DMSO is between 1:2 and 1:100; adding the solution one drop at a time into water with stir at room temperature to form a suspension; collecting the crystalline product of the compound of Formula I from the suspension by filtration in reduced pressure; and obtaining a monohydrate crystalline form of the compound of Formula I after drying.

The disclosure also provides a method of preparing the monohydrate crystalline form of 3-(5-(4-(3-fluoropropyl)piperazin-1-yl)benzimidazol-2-yl)-1-azaazulen-2-one, including: dissolving an amorphous form of 3-(5-(4-(3-fluoropropyl)piperazin-1-yl)benzimidazol-2-yl)-1-azaazulen-2-one of formula I in methanol to form a solution, wherein the weight ratio of the compound of Formula I to the methanol is between 1:50 and 1:500; obtaining a filtrate by filtrating off impurities from the solution; After evaporating the solvent, a monohydrate crystalline form of the compound of Formula I was formed.

The disclosure further provides a pharmaceutical composition including an effective amount of the monohydrate crystalline form of 3-(5-(4-(3-fluoropropyl)piperazin-1-yl)benzimidazol-2-yl)-1-azaazulen-2-one as claimed in claim 1, and at least one pharmaceutically acceptable excipient.

A detailed description is given in the following embodiments with reference to the accompanying drawings.

BRIEF DESCRIPTION OF THE DRAWINGS

The disclosure may be more fully understood by reading the subsequent detailed description and examples with references made to the accompanying drawings, wherein:

FIGS. 10a-10b are a series of diagrams of the monohydrate form of Formula I, illustrating the PK profile in accordance with some embodiments;

DETAILED DESCRIPTION

Figure 1:
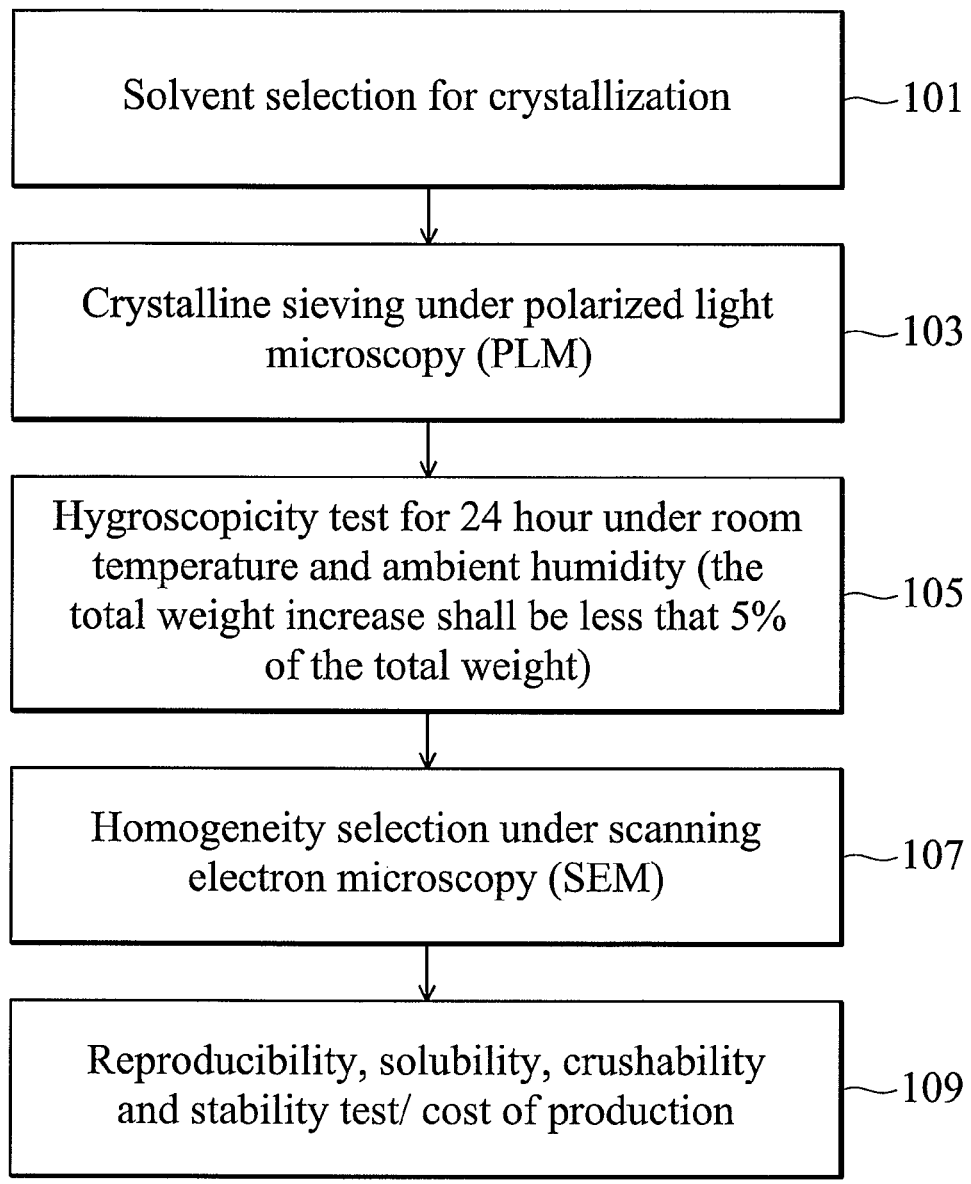
FIG. 1 is a flowchart, showing the process of selecting crystalline forms in accordance with some embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The numerical ranges in this disclosure are approximate, and thus may include values outside of the range unless otherwise indicated. Numerical ranges disclosed herein include all values including the lower and the upper values, and the values therebetween. For example, when referring to 100-500, then all individual values are included, such as 123, 124, 125, etc., and sub ranges, such as 130-180, 180-260, 350-444, etc., are also included.

FIG. 1 shows the screening process of the crystalline forms of the disclosure. First, at step 101, the solubilities of compound 3-(5-(4-(3-fluoropropyl)piperazin-1-yl)benzimidazol-2-yl)-1-azaazulen-2-one of Formula I at 25° C. and 50° C. to 12 representative solvents, including water, dimethyl sulfoxide (DMSO), methanol, acetonitrile, acetone, methyl ethyl ketone, ethanol, ethyl acetate, tetrahydrofuran (THF), 2-propanol, $CH_2Cl_2$, and toluene are analyzed in order to pick out the suitable solvents for crystallization testing by evaporation method, anti-solvent addition method and quench cool of saturated solution method, and the like.

At step 103, 17 crystalline form candidates with homogeneous morphology are selected from the preceding crystallization step by observing with a polarized light microscope.

At next step 105, 15 elected crystalline forms are selected from the hygroscopicity test under room temperature and ambient humidity (the difference of the weight before and after should be less than 5% of the total weight).

After the hydroscopicity testing, 3 crystalline forms with high homogeneity are selected from SEM observation at step 107.

Lastly at step 109, the samples obtained according to the former steps are examined again for their reproducibility, crushability, stability, solubility, in vivo pharmacokinetic profile, and/or other suitable tests, in order to pick out the target crystalline form for the disclosure. After steps 103, 105, 107, and 109, only one of the 17 candidate crystalline forms is reproducible, homogeneous, and satisfies the standard of pharmacokinetic profile testing. The elected crystalline form is monohydrate and is suitable for formulations need such as lozenge, capsule, injection, or the like, and in one embodiment, the capsule type is used.

The compound of Formula I herein may be crystallized into monohydrate by the anti-solvent addition and evaporation crystallized method.

The anti-solvent addition method includes dissolving the amorphous form of the compound of Formula I, 3-(5-(4-(3-fluoropropyl)piperazin-1-yl)benzimidazol-2-yl)-1-azaazulen-2-one, in DMSO. In one embodiment, while stirring and heating to 45-55° C., the compound can be dissolved completely to provide a solution. In one embodiment, the weight ratio of the compound of Formula I to DMSO may be between 1:2 and 1:100. In another embodiment, the heating temperature may be about 50° C. and the weight ratio may be about 1:10. The solution is then added slowly into water at room temperature to form a suspension and it may be stirred continuously for a period of time, such as 10-20 hours, in order to increase the crystallization yield, in accordance with some embodiments. Then filtration in reduced pressure may be applied to the suspension with 5-10 mL of water washing away impurities and the crystalline product may thus be generated. In one embodiment, the crystalline product of the compound of Formula I may be dried, for example oven-dried at about 40-50° C., to obtain the monohydrate crystalline form. In one embodiment, the drying temperature may be about 45° C.

The evaporation method includes dissolving the amorphous form of the compound of Formula I, 3-(5-(4-(3-fluoropropyl)piperazin-1-yl)benzimidazol-2-yl)-1-azaazulen-2-one, in methanol. In one embodiment, while stirring and heating to 70-90° C., the compound can be dissolved completely to provide a solution. In one embodiment, the weight ratio of the compound of Formula I to DMSO may be between 1:50 and 1:500. In another embodiment, the heating temperature may be about 80° C. and the weight ratio may be about 1:400. The solution may then be filtrated and left standing in the hood at room temperature for a period of time for votalization of the methanol and to form the crystalline product. At the same time, any additional solvent left may also be removed by suction, in accordance with some embodiments. In one embodiment, the crystalline product of the formula I may be dried, for example, oven-dried at about 40-50° C. or at room temperature, to obtain the monohydrate crystalline form. In one embodiment, the drying temperature may be about 45° C.

In one embodiment, the monohydrate form of 3-(5-(4-(3-fluoropropyl)piperazin-1-yl)benzimidazol-2-yl)-1-azaazulen-2-one analyzed by x-ray powder diffraction exhibit characteristic peaks at 2 θ angles of 12.9°, 15.9°, 17.9°, 21.2°, 22.9°, 23.5° and 24.5° (±0.4°) when analyzed by powder X-ray diffraction (PXRD). The observed PXRD pattern is reproduced as FIG. 2 and the peak listing is provided in Table 1 below, which includes only the peaks with peaks intensity more than 10%. In Table 1, "2 θ" represents the diffraction angle and the intensity is defined by the relative proportional percentage to the maximum peak (I/II).

TABLE 1

XRPD data of monohydrate form of Formula I

| 2θ | intensity(%) |
|---|---|
| 12.67° | 15.4 |
| 12.94° | 22.7 |
| 13.76° | 12.7 |
| 15.85° | 32.7 |
| 17.92° | 100 |
| 21.23° | 14.9 |
| 22.87° | 17.5 |
| 23.48° | 30.9 |
| 24.51° | 78.3 |
| 25.21° | 15.4 |
| 29.19° | 12.5 |

Figure 3:
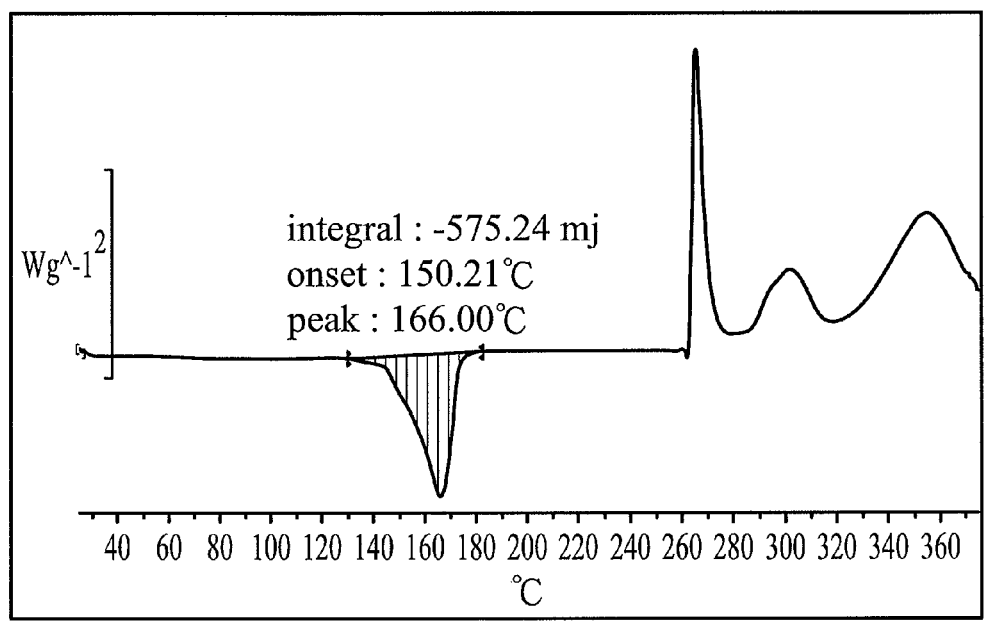
FIG. 3 is a DSC curve of the monohydrate form of Formula I in accordance with some embodiments.

In another embodiment, the monohydrate form of 3-(5-(4-(3-fluoropropyl)piperazin-1-yl)benzimidazol-2-yl)-1-azaazulen-2-one analyzed by differential scanning calorimetry shows a sharp, melting endothermic peak at 260° C. (±5° C.) and a dehydration endothermic peak at 130-180° C. (±10° C.), as shown in FIG. 3.

Figure 4:
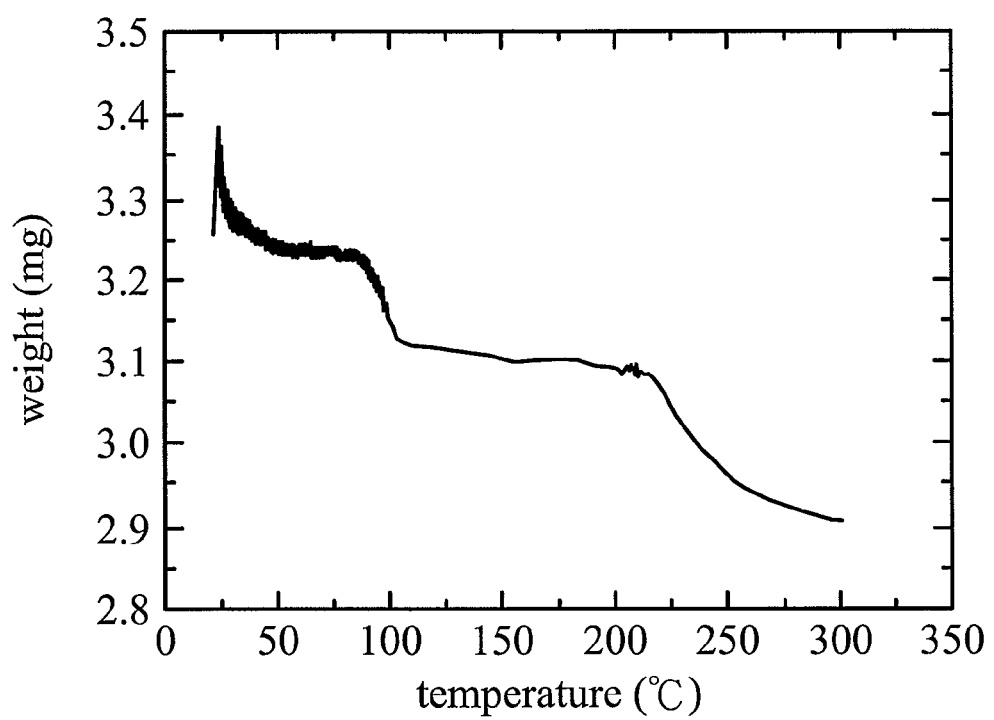
FIG. 4 is a thermogravimetric diagram of the monohydrate form of Formula I in accordance with some embodiments.

In further embodiment, the monohydrate form of 3-(5-(4-(3-fluoropropyl)piperazin-1-yl)benzimidazol-2-yl)-1-azaazulen-2-one analyzed by thermogravimetric analysis, as shown in FIG. 4, exhibits a dehydration at 80-155° C. with a weight loss of about 4.1%.

Figure 5:
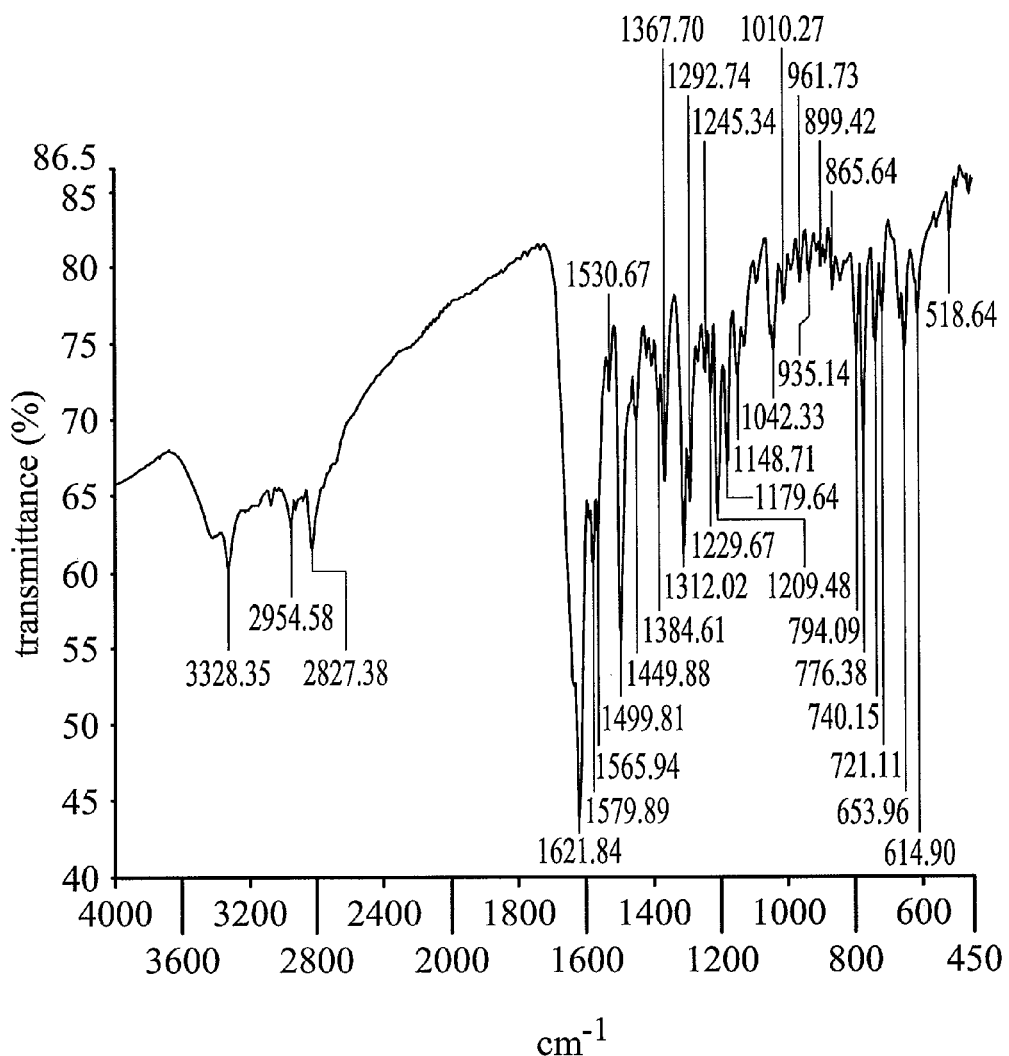
FIG. 5 is an IR spectrum of the monohydrate form of Formula I in accordance with some embodiments.

In a further embodiment, the monohydrate form of 3-(5-(4-(3-fluoropropyl)piperazin-1-yl)benzimidazol-2-yl)-1-azaazulen-2-one analyzed with infrared spectroscopy exhibits characteristic peaks at 3328, 2827, 1622, 1500, 1312, 1209, and 776 cm$^{-1}$ (±0.5 cm$^{-1}$), and the intensity is a relative value compared to the major peak of the spectrum, as shown in FIG. 5.

According to the DSC analysis, the melting point of the monohydrate form of 3-(5-(4-(3-fluoropropyl)piperazin-1-yl)benzimidazol-2-yl)-1-azaazulen-2-one is about 260° C. (±5° C.). In another embodiment, the solubility of the monohydrate form of 3-(5-(4-(3-fluoropropyl)piperazin-1-yl)benzimidazol-2-yl)-1-azaazulen-2-one in different pH solution is proceed by the steps: placing a sample into each of the buffer solutions with a pH value of 1.2, 5, 6.8, and 7.4, oscillating the buffer solutions in an incubator at 300 rpm for 24 hours, and analyzing with high-performance liquid chromatography. The result is shown in Table 2.

TABLE 2

| Formula (I) | Concentration (μg/mL) |
|---|---|
| pH1.2 | 26315.6 |
| pH5 | 263.1 |
| pH6.8 | 3.7 |
| pH7.4 | 2.4 |

In general, any drug substance must be formulated to a suitable dosage form according to the intended route of administration. The most popular pharmaceutical formulation is a tablet or capsule, such a dosage form being easily and conveniently administered via the oral route. For formulation as a tablet or capsule, a drug substance should be non-hygroscopic and compressible. Hygroscopicity may lead to processing problems and a short shelf life. Water uptake during processing steps may lead to poor flow characteristics (i.e. sticking or change of material strength). A suitable drug substance should also possess solubility and a rate of dissolution that leads to rapid bioavailability on exposure to the gastric environment.

The pharmaceutical composition of the embodiments contains an effective amount of the monohydrate form of Formula I and a pharmaceutically acceptable excipient or salt. The pharmaceutically acceptable excipient may include solvents, dispersion media, coatings, antibacterial and antifungal agents, isotonic and absorption delaying agents, and the like. Other than the aforementioned methods of administering to a subject (e.g., a mammal), it may also be administered parenterally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

"An effective amount" refers to a non-toxic but sufficient amount of the drug to provide the desired therapeutic or prophylactic effect. The effective amount of the monohydrate form of the azaazulene compound in the disclosure means an amount that will provide the desired inhibitive effect on protein kinases.

A sterile injectable composition may be a solution or suspension in a non-toxic parenterally acceptable diluent or solvent, such as a solution in 1,3-butanediol. Among the acceptable vehicles and solvents that may be employed are mannitol, water, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivative, are useful in the preparation of injectables, as are natural pharmaceutically acceptable oils, such as olive oil or castor oil, especially in their polyoxyethylated forms. These oil solutions or suspensions may also contain a long-chain alcohol diluents or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms may also be used for the purpose of formulation.

A composition for oral administration may be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in capsule form, useful diluents include lactose and dried corn starch. When aqueous suspensions or emulsions are administered orally, the active ingredient may be suspended or dissolved in an oily phase combined with emulsifying or suspending agents. If desired, certain sweetening, flavoring, or coloring agents may be added.

A nasal aerosol or inhalation composition may be prepared according to techniques well known in the art of pharmaceutical formulation. For example, such a composition may be prepared as a solution in saline, employing benzyl alcohol or other suitable preservatives, absorption promoters to enhance bioavailability, fluorocarbons, and/or other solubilizing or dispersing agents known in the art.

A composition having the monohydrate form of Formula I may also be administered in the form of suppositories for rectal administration.

The excipient in the pharmaceutical composition must be "acceptable" in the sense that it is compatible with the active ingredient of the composition (and preferably, capable of stabilizing the active ingredient) and not deleterious to the subject to be treated. One or more solubilizing agents may be utilized as pharmaceutical excipients for delivery of the monohydrate form of Formula I. Examples of other carriers include colloidal silicon oxide, magnesium stearate, cellulose, sodium lauryl sulfate, and D&C Yellow 10.

The monohydrate form of Formula I described above may be preliminarily screened for their efficacy in treating the diseases described above by in vitro assays and then confirmed by animal experiments and clinic trials. Other methods will also be apparent to those with ordinary skill in the art.

The embodiments also provide a method of inhibiting the activity of protein kinase or protein phosphatase in a cell with the monohydrate form of Formula (I) described above. The method includes contacting cells expressing protein kinase or phosphatase with such a monohydrate form of Formula I. Protein kinase and phosphatase regulate signaling cascades. The cascades in turn regulate cell growth, migration, differentiation, gene expression, muscle contraction, glucose metabolism, cellular protein synthesis, and regulation of the cell cycle.

The term "protein kinase" refers to a kinase enzyme that modifies other proteins by chemically adding phosphate groups to them (phosphorylation). Examples of the protein kinase includes, but are not limited to, 5' adenosine monophosphate-activated protein kinase (AMPK), B lymphocyte kinase (BLK), Colony stimulating factor 1 receptor (CSF1R), Fibroblast growth factor receptor (FGFR), fibroblast factor receptor (FFR), fms-like tyrosine kinase-3 (FLT3), kinase insert domain receptor (KDR), tyrosine-protein kinase KIT (KIT), lymphocyte cell-specific protein-tyrosine kinase (LCK), tyrosine-protein kinase LYN (LYN), mitogen activated protein kinase kinase kinase kinase 5 (MAP4K5), neurotrophic tyrosine receptor kinase (NTRK), phosphorylase kinase gamma 1 (PHKG1), RET-oncogene (RET), steroid receptor coactivator (SRC), serine/threonine kinase (STK), and Yamaguchi sarcoma viral oncogene homolog 1 (YES1).

The specific examples below are to be construed as merely illustrative, and not limiting to the remainder of the disclosure in any way whatsoever. Without further elaboration, it is believed that one skilled in the art may, based on the description herein, utilize the present disclosure to its fullest extent. All publications cited herein are hereby incorporated by reference in their entirety.

As will be appreciated by the skilled person, the relative intensities of the various peaks within Table 1 may vary due to a number of factors such as, for example orientation effects of crystals in the X-ray beam or the purity of the material being analyzed or the degree of crystallinity of the sample. The peak positions may also shift for variations of sample height but the peak positions will remain substantially as defined in Table 1. The skilled person will also appreciate that measurements using a different wavelength will result in different shifts according to the Bragg equation (nλ=2d sin θ). Such further PXRD patterns generated by use of alternative wavelengths are alternative representations of the PXRD patterns of the crystalline materials of the embodiments.

EXAMPLE

Example 1

Anti-Solvent Addition Method

The amorphous form of azaazulene of Formula I (7.09 g) was added to DMSO (about 71 mL). The solution was then stirred and heated to about 50° C. for complete dissolution. The solution was added drop by drop to water (141 mL) with stir at room temperature. After 16 hours of stirring, filtration in reduced pressure was performed and washed with water (10 mL) to remove impurities. Finally, the resulting product was oven-dried at 45° C. and the monohydrate form of Formula I (6.8 g) was obtained in 96% yield.

Example 2

Evaporation Method

The amorphous form of azaazulene of Formula I (200.9 mg) was added to methanol (about 100 mL). The solution was then stirred and heated to about 80° C. for complete dissolution. The solution was filtrated to remove the impurities and then cooled in the hood for crystallization at least 36 hours. Finally, any remaining methanol was sucked away and the resulting product was oven-dried at 45° C. to obtain of the monohydrate form of Formula I (171.7 mg) in 85% yield.

Example 3

XRPD Analysis

Figure 2:
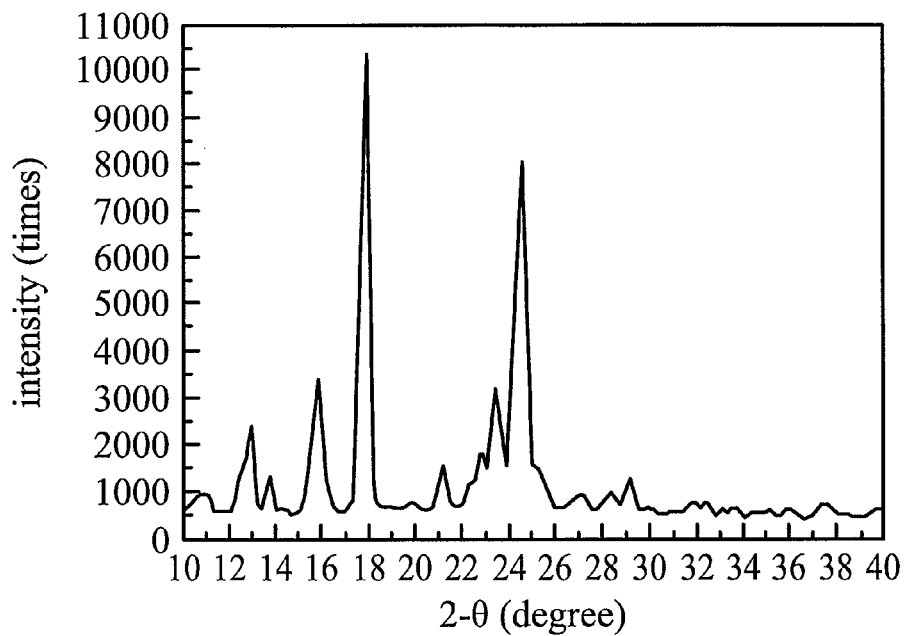
FIG. 2 is a XRPD diagram of the monohydrate form of Formula I in accordance with some embodiments.

The powder X-ray diffraction pattern for Formula I was determined using a Bruker-AXS Ltd D2 powder X-ray diffractometer. The specimen was rotated whilst being irradiated with copper K-alpha$_1$ X-rays (wavelength=1.5406 Angstroms) with the X-ray tube operated at 30 kV/10 mA. The analysis was performed with the goniometer running in continuous mode set for a 0.2 second count per 0.03° step over a two theta range of 10°-40°. The results are shown in FIG. 2.

Example 4

DSC Analysis

In the experiments conducted in order to accumulate the DSC data described above, the samples of monohydrate form of Formula I were heated from 25 to 320° C. at 10° C. per minute using a DSC 822e system (Mettler Toledo, Switzerland) in an aluminum pan and lids, with a nitrogen purge gas. The results are shown in FIG. 3.

Example 5

TGA Analysis

Thermal gravimetric analysis was performed using a Pt-1600 system (Linseis) fitted with an automatic sample changer. Approximately 3.26 mg of the sample was accurately weighed into a Pt 10%/Pt-Rh pan. The sample was heated at 5° C./minute over the range 22.3° C.-300° C. with a nitrogen gas purge. The results are shown in FIG. 4.

Example 6

Infrared Spectroscopy

The infrared spectrum was acquired using a Perkin-Elmer Spectrum One FT-IR spectrometer fitted with a diamond/ZnSe Universal ATR accessory. The sample was prepared by placing about 1 mg of sample of monohydrate form of Formula I on the diamond ATR crystal and ensuring good crystal sample contact. The spectrum was recorded at 2 cm$^{-1}$ resolution.

Characteristic peaks were recorded at 3328, 2827, 1622, 1500, 1312, 1209, and 776 cm$^{-1}$ (±0.5 cm$^{-1}$). The results are shown in FIG. 5.

Example 7

Reproducibility Test

The monohydrate form of Formula I was remade three times as Sample 2, Sample 3, and Sample 4, and the three samples were analyzed by XPRD analysis to obtain their respective characteristic peaks for comparison with FIG. 2.

Figure 6A:
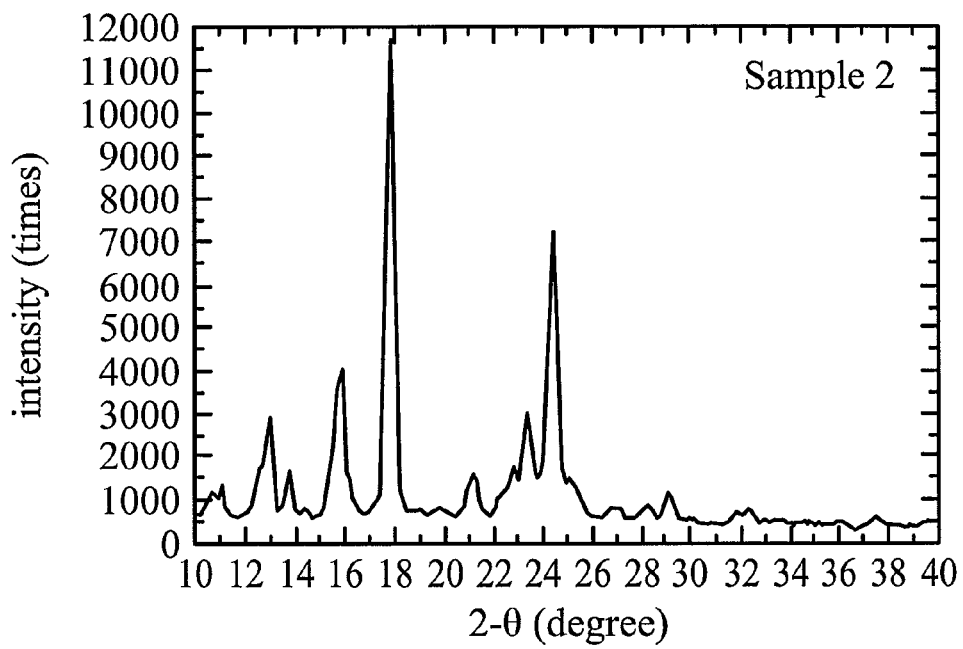
FIGS. 6a-6c are a series of X-ray diffractograms of the monohydrate form of Formula I, showing the results of reproducibility testing in accordance with some embodiments.
Figure 6B:
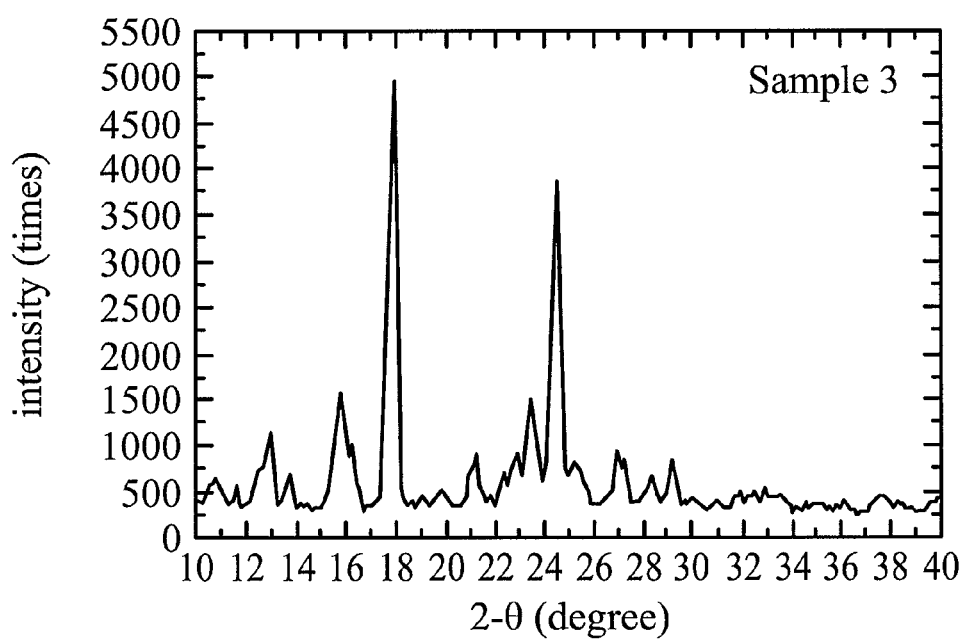
Figure 6C:
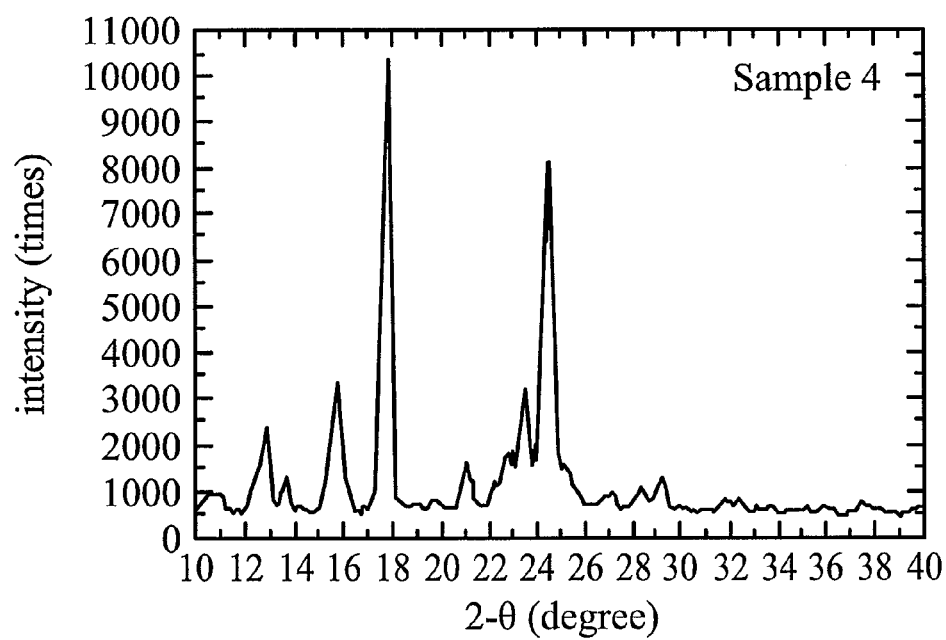

The results are shown in FIGS. 6a-6c, the results of samples 2, 3 and 4 were substantially the same as the original sample. There was no statistically significant difference, which suggests that the monohydrate form of Formula I was reproducible.

Example 8

Stability Test

Figure 7A:
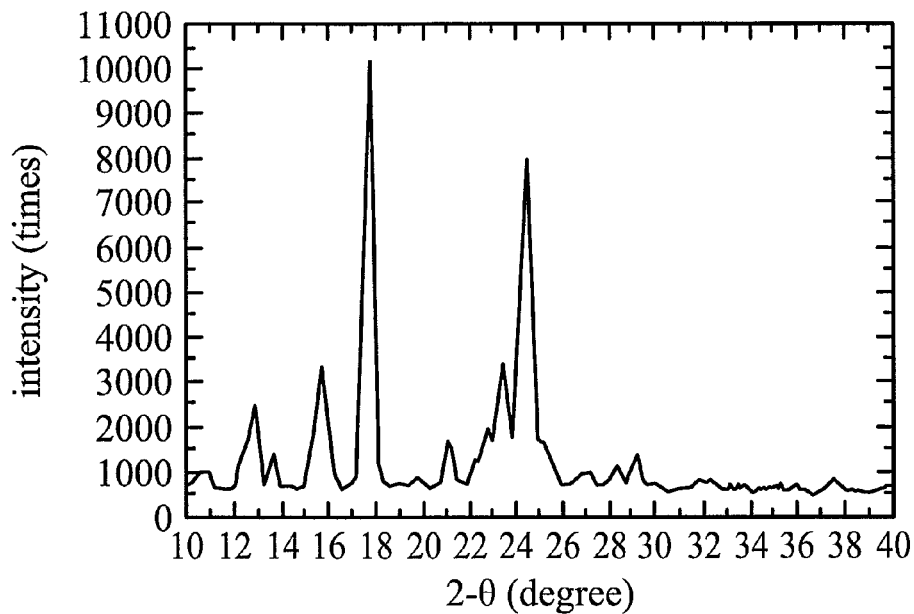
FIGS. 7a-7d are a series of X-ray diffractograms of the monohydrate form of Formula I, showing the results of stability testing in accordance with some embodiments.
Figure 7B:
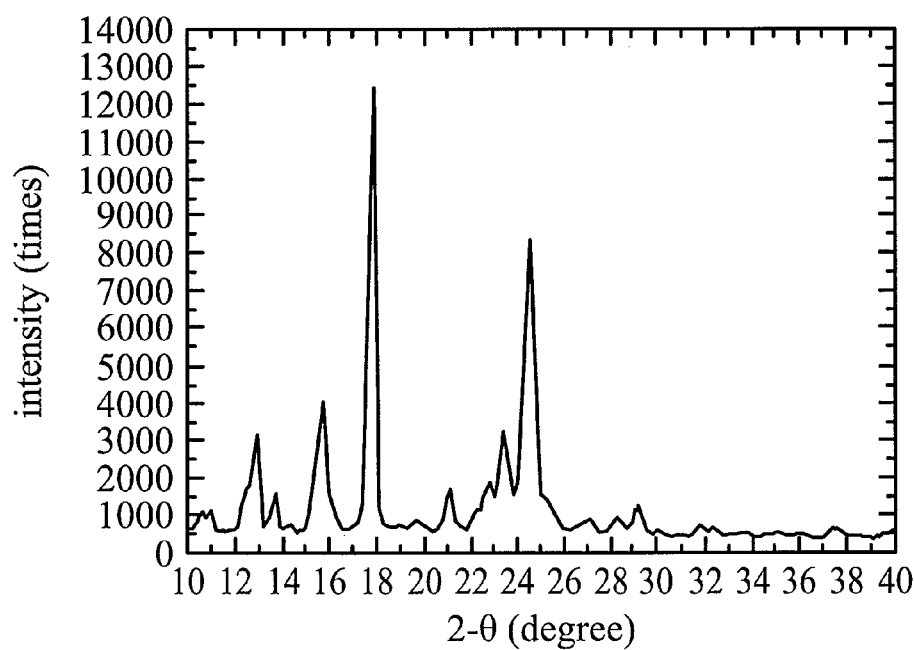
Figure 7C:
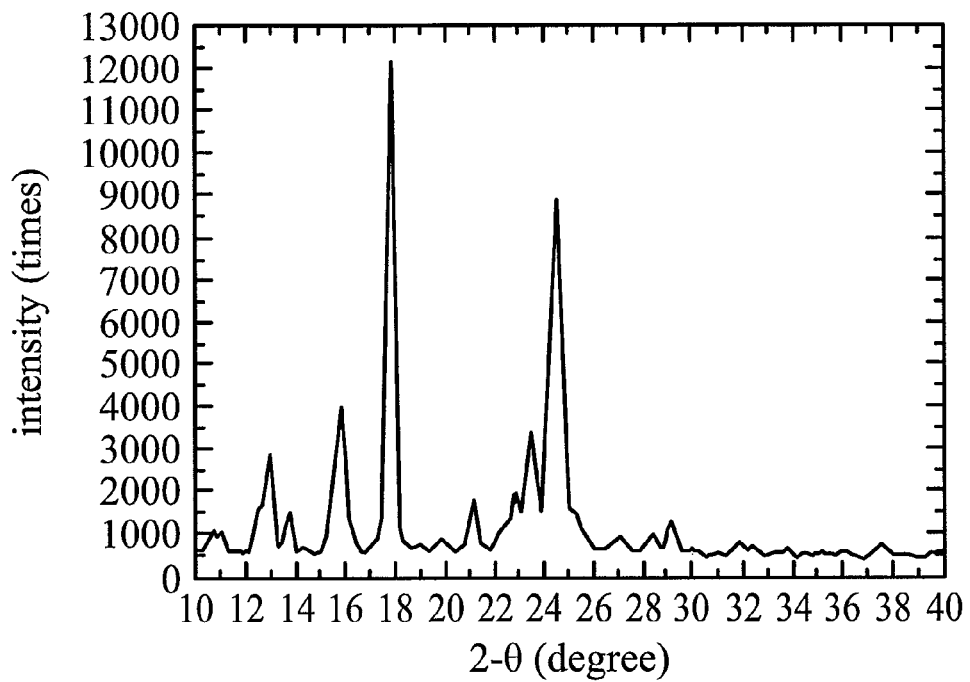
Figure 7D:
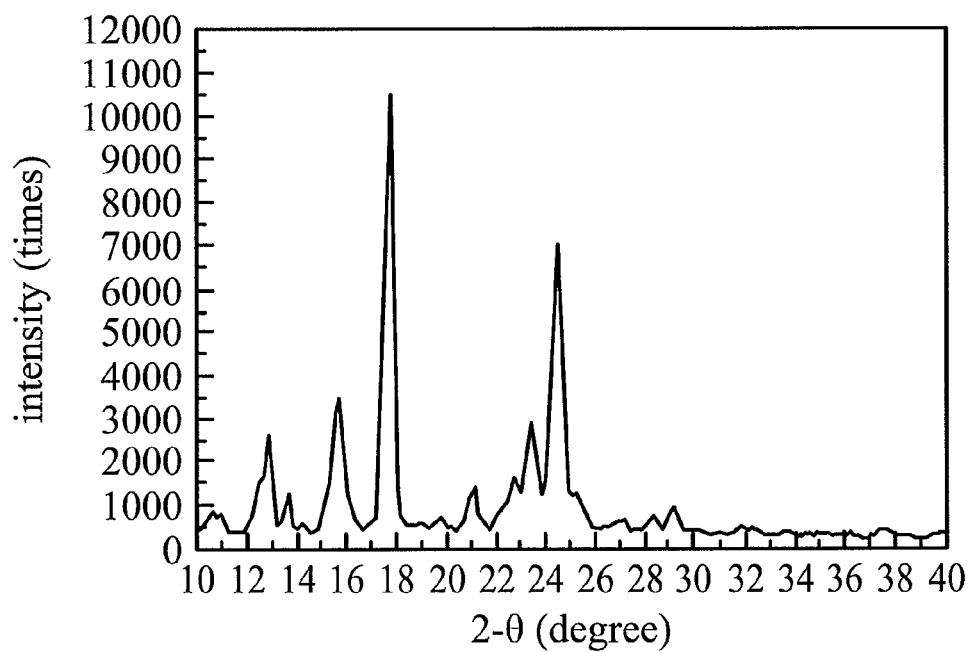
Figure 8A:
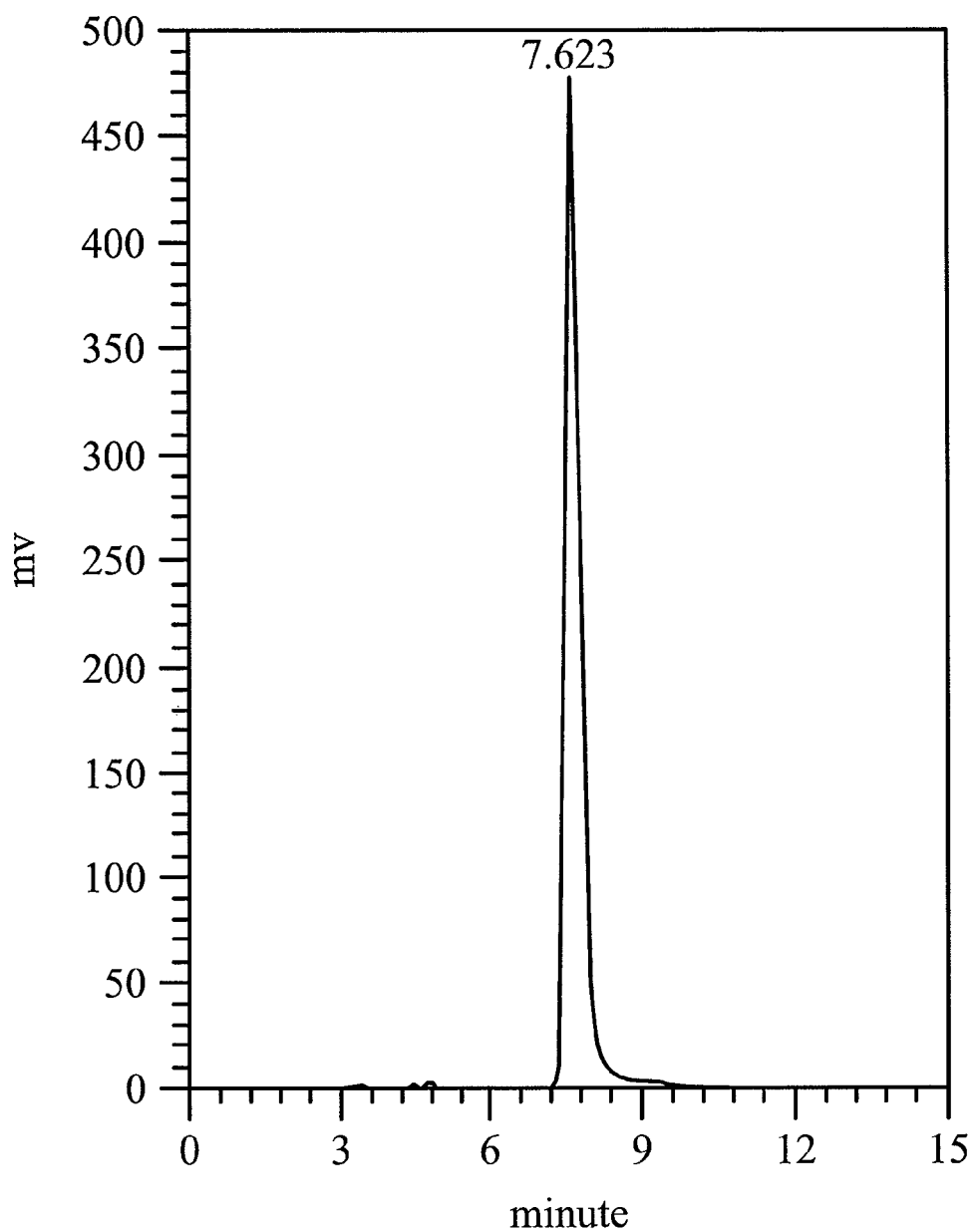
FIGS. 8a-8d are a series of X-ray diffractograms of the monohydrate form of Formula I, also showing some results of stability testing in accordance with some embodiments.
Figure 8B:
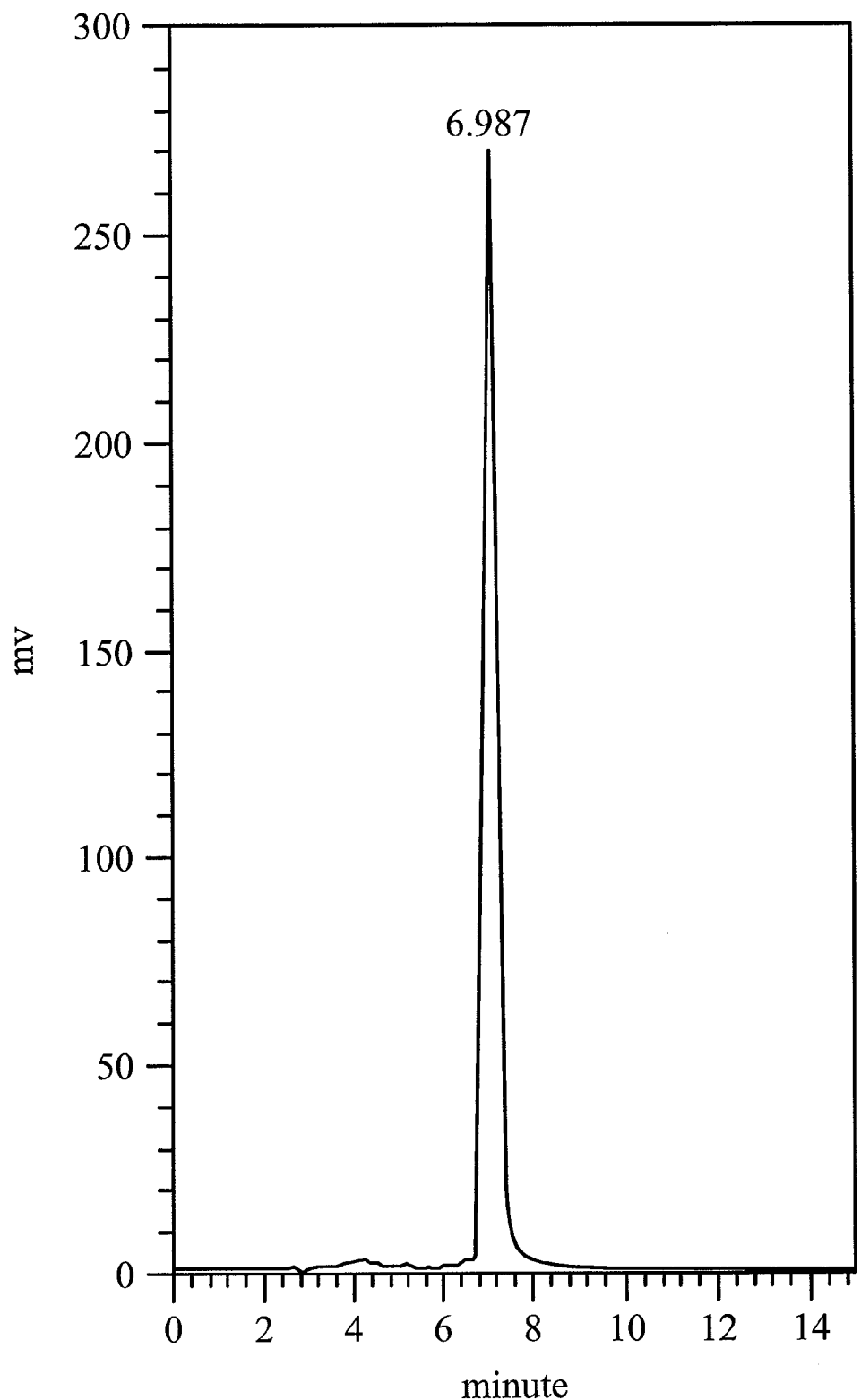
Figure 8C:
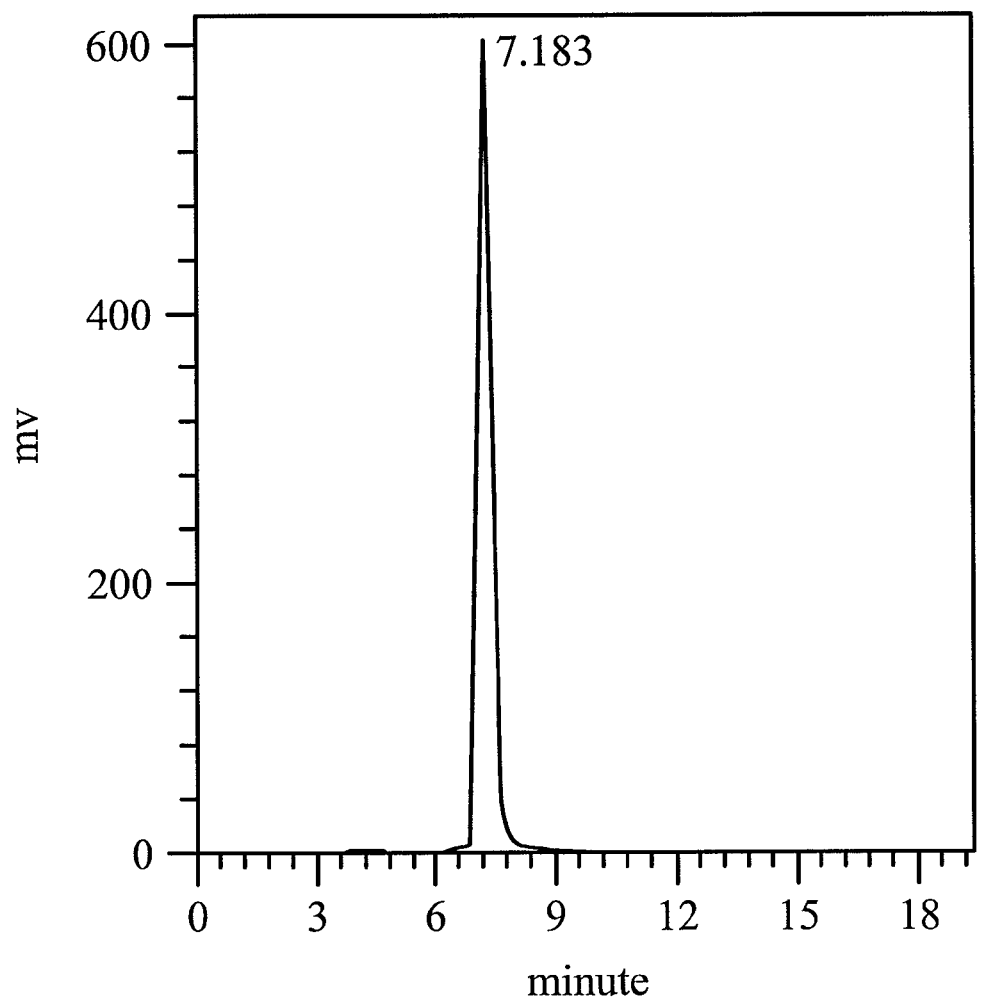
Figure 8D:
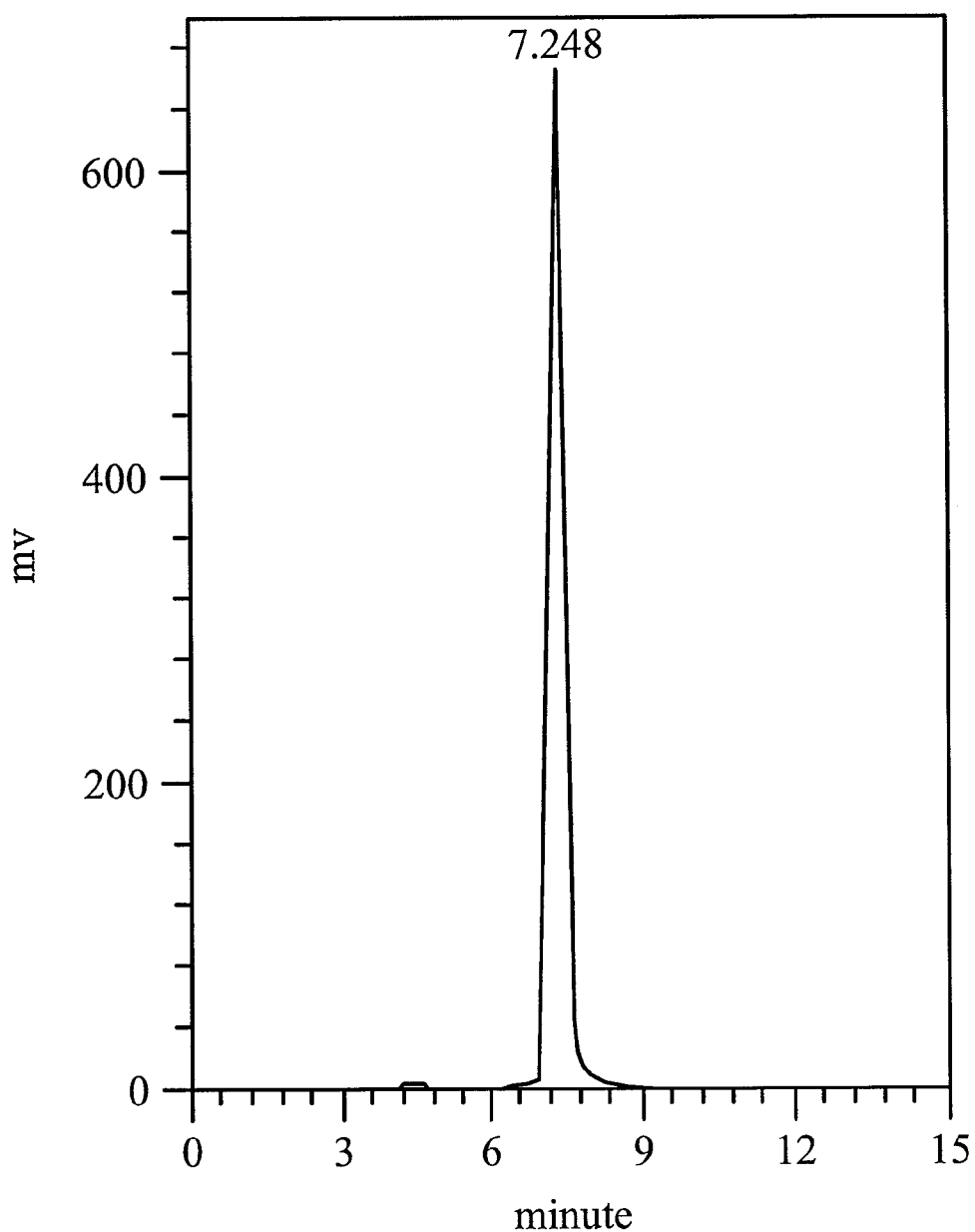

An appropriate amount of samples were prepared according to the method of Example 1. A XPRD analysis and a HPLC analysis were performed, under the environment of about 25-30° C. and 40%-45% RH, after the preparation of the samples (FIGS. 7a and 8a), and after one month (FIGS. 7b and 8b), two months (FIGS. 7c and 8c), and four months (FIGS. 7d and 8d) respectively from the time of preparation, and the results were examined to observe their differences over time.

The results are shown in FIGS. 7a-7d and 8a-8d. There was no statistically significant difference, showing that the samples under the above environment mentioned were stable and substantially the same over four months.

Example 9

Stability Examination by Slurry Test

1. Formula I-EA: the monohydrate form of Formula I (57 mg) and Ethyl acetate (1 mL) was provided.
2. Formula I-Heptane: the monohydrate form of Formula I (51 mg) and Heptanes (1 mL) was provided:
3. Formula I-IPA: the monohydrate form of Formula I (53 mg) and 1 mL of Isopropanol (1 mL) was provided.

Figure 9A:
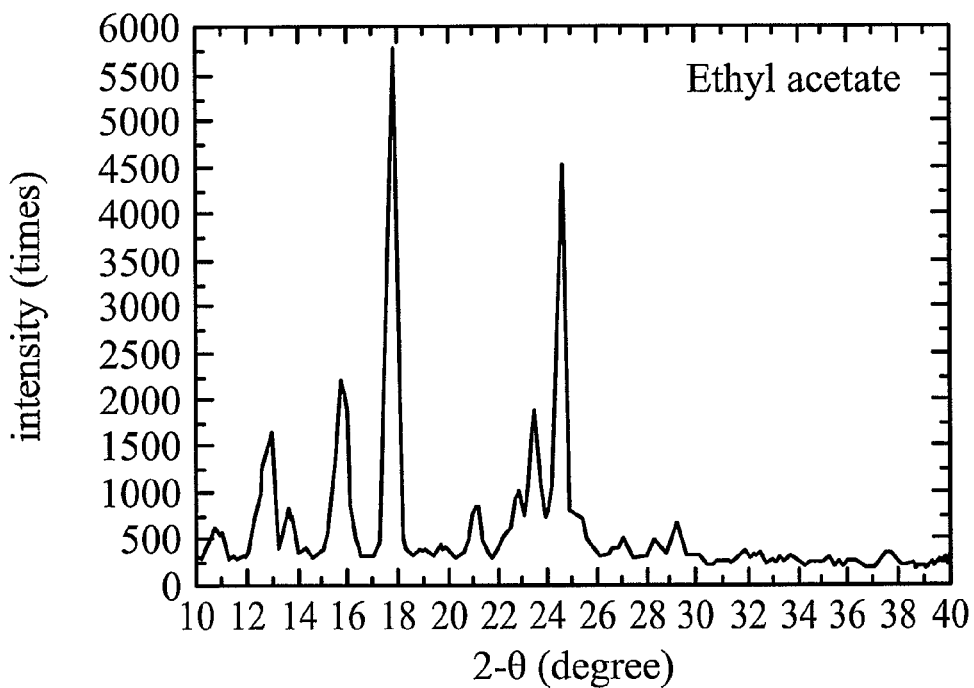
FIGS. 9a-9c are a series of X-ray diffractograms of the monohydrate form of Formula I, showing some other results of stability testing in accordance with some embodiments.
Figure 9B:
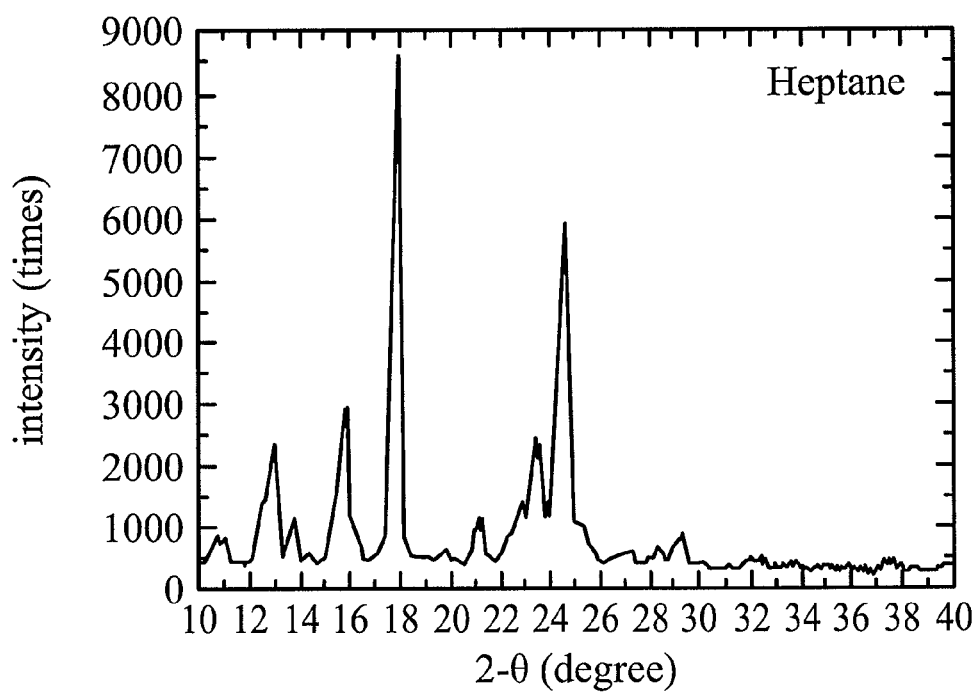
Figure 9C:
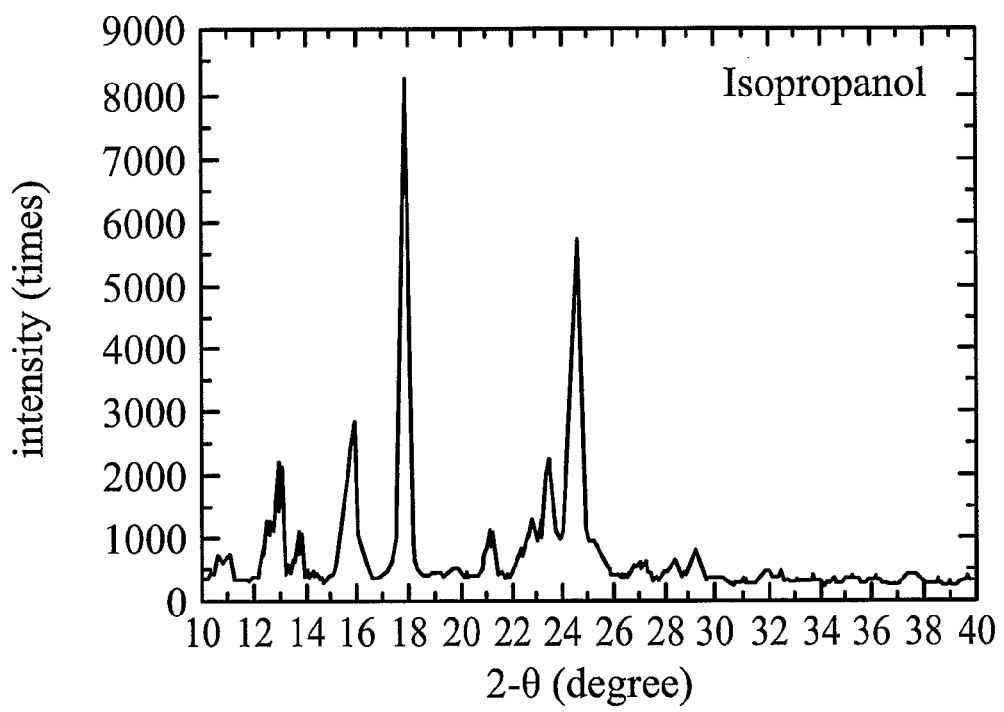

The solutions provided above were stirred at 25° C. for 3 days and then a centrifugation was performed to collect the solid with centrifuge in each. Each of the collected solids was dried and analyzed using XPRD. The results are shown in FIGS. 9a-9c. Compared to the XRPD analysis of the original crystalline form as shown in FIG. 2, there was no statistically significant difference, showing that the crystalline form of the disclosure is stable. This is a pre-test for the subsequent formulation, which is aimed to confirm that the monohydrate form wouldn't change with the incorporation of solvents. Therefore, the solvents used herein may not be the same as those crystallized solvents used in the embodiments.

Example 10

Pharmacokinetics Profile (PK Profile)

The pharmacokinetics profile and the bioavailability were tested by a PO (per os) dosing with 30 mg/kg of sample of Example 1 (monohydrate), good in capsule (Tropac, 9el) and in bottle (0.5% methyl cellulose suspension) for male SD rat; and also a PO dosing with 30 mg/kg of sample #4 (mixed crystalline form) in 0.5% methyl cellulose for male SD rat as a treatment control. With the result from the above testing, the preferable PO dosing for first in human model was determined.

Figure 10B:
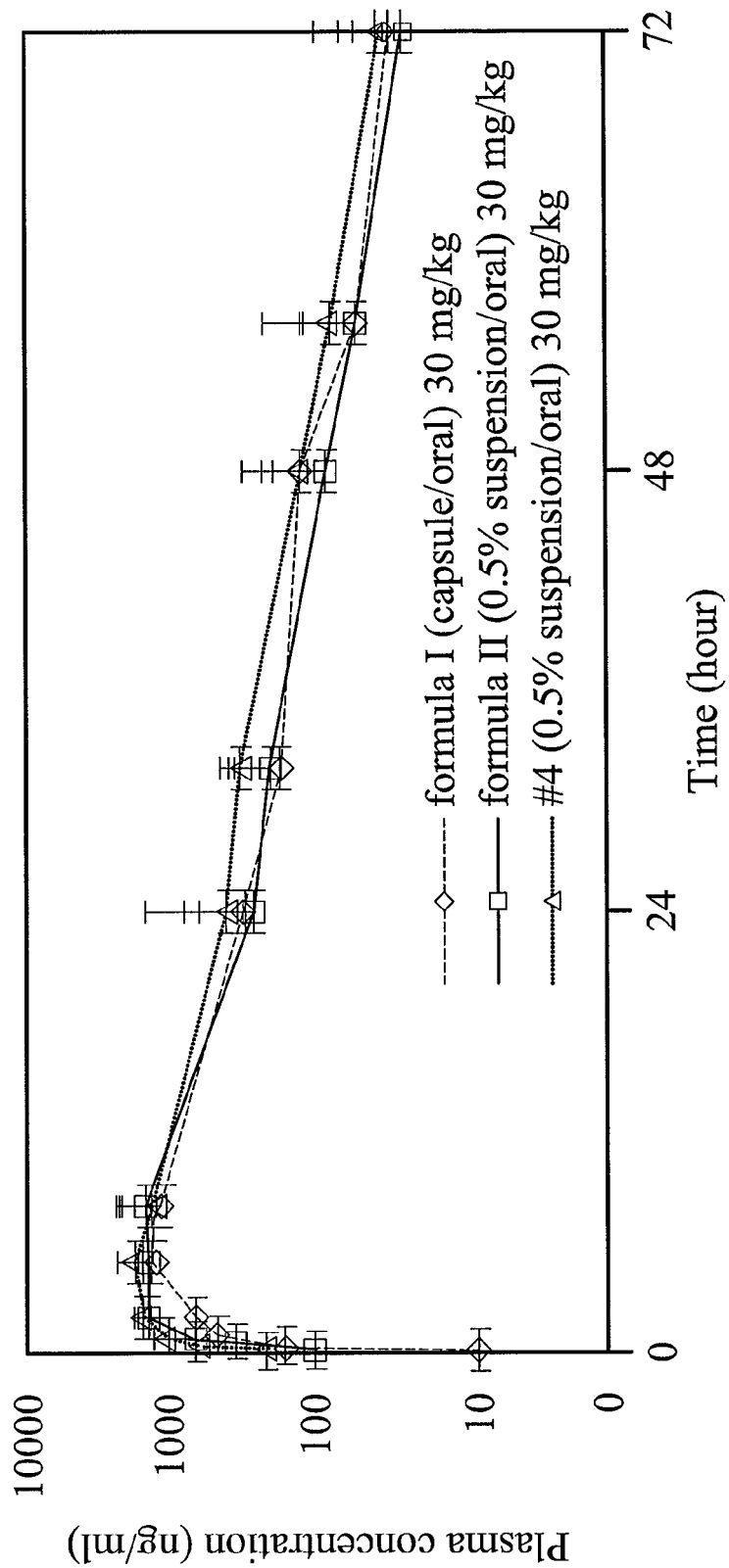

Generally, the PK profile of the crystalline form with good crystallinity and stability would be worse than that of amorphous form and complex form. But according to the PK profile result shown in FIG. 10a and FIG. 10b, there was no statistically significant difference between the 3 treatments, which means that 1) the monohydrate form of Formula I was a qualified crystalline form with bioavailability and could be metabolized normally; 2) the capsule formulation was a preferable PO application method.

The terms used in FIG. 10 were listed as follows, PO (per os) represents taken by mouth; $C_{max}$ (ng/mL) represents the peak plasma concentration of a drug after administration; $T_{max}$ (hr) represents the time to reach $C_{max}$; $T_{1/2}$ (hr) represents elimination half-life, which represents the time required for the concentration of the drug to reach half of its original value; and AUC (hr*ng/mL) [area under the curve] represents the integral of the concentration-time curve (after a single dose or in steady state), and the bioavailability could be deducted from AUC values.

Comparative Example

Anhydrate Form of Formula I

The monohydrate form of Formula I (300 mg) was dissolved at room temperature in the mix solution of $CH_2Cl_2$ (50 mL) and methanol (50 mL). $Na_2SO_4$ (10 g) was then added into the solution to absorb water with stir for 2 hours. The stirred solution was filtrated in reduced pressure to collect the anhydrate form sample of Formula I. The sample was analyzed by XPRD and Hydroscopicity test, showing that the anhydrate form has a higher hygroscopicity (3.81%) than that of the monohydrate form of Formula I (1.57%).

Figure 11:
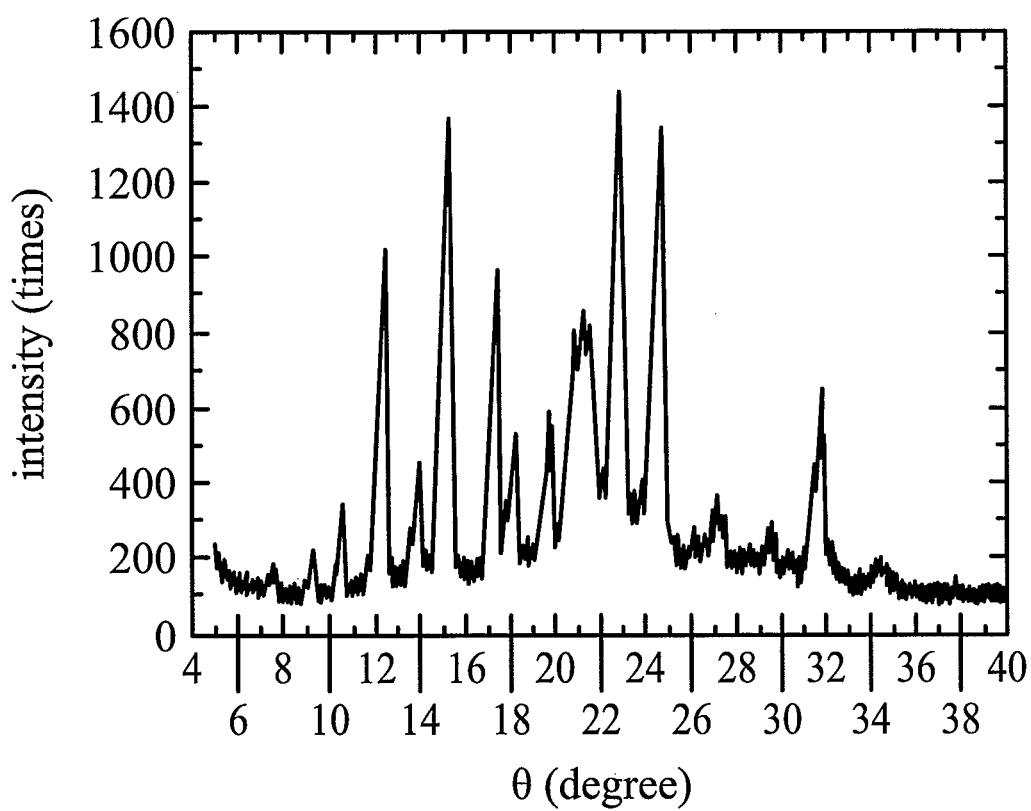
FIG. 11 is a X-ray diffractogram of the anhydrate form of Formula I in accordance with some embodiments.

The results are shown in FIG. 11 and Table 3 below.

TABLE 3

|  | monohydrate form | | anhydrate form (comparative example) | |
|---|---|---|---|---|
| Time | 1 day | | 1 day | |
| Temperature(° C.) | 22.5 | 21.8 | 22.5 | 21.8 |
| Relative humidity (%) | 70 | 71 | 70 | 71 |
| Weight gain (%) | 1.57 | | 3.81 | |

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A monohydrate crystalline form of 3-(5-(4-(3-fluoropropyl)piperazin-1-yl)benzimidazol-2-yl)-1-azaazulen-2-one,

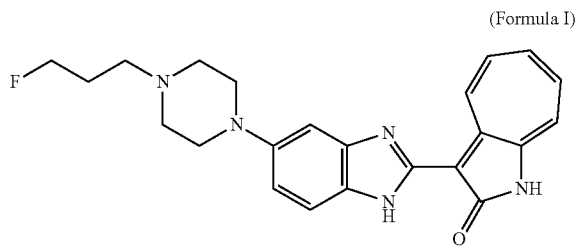 [SMILES: O=c1[nH]c2cccccc-2c1-c1nc2cc(N3CCN(CCCF)CC3)ccc2[nH]1]

(Formula I)

possesses diffraction peaks of about 12.9°, 15.9°, 17.9°, 21.2°, 22.9°, 23.5° and 24.5°.

2. The monohydrate crystalline form of 3-(5-(4-(3-fluoropropyl)piperazin-1-yl)benzimidazol-2-yl)-1-azaazulen-2-one as claimed in claim 1, which exhibits a dehydration endothermic peak at about 130-180° C., and a melting endothermic peak at about 260° C. in a differential scanning calorimetry (DSC) thermogram.

3. The monohydrate crystalline form of 3-(5-(4-(3-fluoropropyl)piperazin-1-yl)benzimidazol-2-yl)-1-azaazulen-2-one as claimed in claim 1, which exhibits dehydration at about 80-155° C. with a weight loss 4.1% in a thermogravimetric analysis (TGA).

4. The monohydrate crystalline form of 3-(5-(4-(3-fluoropropyl)piperazin-1-yl)benzimidazol-2-yl)-1-azaazulen-2-one as claimed in claim 1, which exhibits characteristic absorptions expressed in $cm^{-1}$ at: 3328, 2827, 1622, 1500, 1312, 1209, and 776 in an infrared spectrum.

5. The monohydrate crystalline form of 3-(5-(4-(3-fluoropropyl)piperazin-1-yl)benzimidazol-2-yl)-1-azaazulen-2-one as claimed in claim 1, having an X-ray diffractogram substantially in accordance with FIG. 2.

6. The monohydrate crystalline form of 3-(5-(4-(3-fluoropropyl)piperazin-1-yl)benzimidazol-2-yl)-1-azaazulen-2-one as claimed in claim 2, having a DSC curve substantially in accordance with FIG. 3.

7. The monohydrate crystalline form of 3-(5-(4-(3-fluoropropyl)piperazin-1-yl)benzimidazol-2-yl)-1-azaazulen-2-one as claimed in claim 3, having a thermogravimetric diagram substantially in accordance with FIG. 4.

8. The monohydrate crystalline form of 3-(5-(4-(3-fluoropropyl)piperazin-1-yl)benzimidazol-2-yl)-1-azaazulen-2-one as claimed in claim 4, having an IR spectrum substantially in accordance with FIG. 5.

9. A method of preparing a monohydrate crystalline form of 3-(5-(4-(3-fluoropropyl)piperazin-1-yl)benzimidazol-2-yl)-1-azaazulen-2-one, as claimed in claim 1, comprising:
dissolving an amorphous form of 3-(5-(4-(3-fluoropropyl)piperazin-1-yl)benzimidazol-2-yl)-1-azaazulen-2-one of Formula I in dimethyl sulfoxide to form a solution, wherein the weight ratio of the compound of Formula I to DMSO is between 1:2 and 1:100; adding the solution one drop at a time into a water stirred at room temperature to form a suspension; collecting the crystalline product of the compound of Formula I from the suspension by suction filtration; and obtaining a monohydrate form of the compound of Formula I by drying the crystalline product.

10. The method as claimed in claim 9, wherein the ratio of the compound of Formula I to DMSO is 1:10.

11. The method one as claimed in claim 9, wherein the dissolving of the compound of Formula I in DMSO is carried out at a temperature of 45-55° C. while stirring.

12. The method as claimed in claim 9, wherein the dissolving of the compound of Formula I in DMSO is carried out at a temperature of about 50° C. while stirring.

13. A method of preparing a monohydrate crystalline form of 3-(5-(4-(3-fluoropropyl)piperazin-1-yl)benzimidazol-2-yl)-1-azaazulen-2-one, as claimed in claim 1, comprising:
dissolving an amorphous form of 3-(5-(4-(3-fluoropropyl)piperazin-1-yl)benzimidazol-2-yl)-1-azaazulen-2-one of formula I in methanol to form a solution, wherein the weight ratio of the compound of Formula I to methanol is between 1:50 and 1:500; obtaining a filtrate by filtrating off impurities from the solution; evaporating the methanol to form a crystalline product by leaving the filtrate to stand; and obtaining a monohydrate form of the compound of Formula I by drying the crystalline product.

14. The method as claimed in claim 13, wherein the ratio of the Formula I compound to methanol is 1:400.

15. The method as claimed in claim 13, wherein the dissolving of the compound of Formula I in to methanol is carried out at 70-90° C. while Stirring.

16. The method as claimed in claim 13, wherein the dissolving of the compound of Formula I in methanol is carried out at about 80° C. while stirring.

17. A pharmaceutical composition comprising an effective amount of a monohydrate crystalline form of 3-(5-(4-(3-fluoropropyl)piperazin-1-yl)benzimidazol-2-yl)-1-azaazulen-2-one as claimed in claim 1, and at least one pharmaceutically acceptable excipient.

* * * * *